United States Patent [19]
Takeo

[11] Patent Number: 6,125,166
[45] Date of Patent: Sep. 26, 2000

[54] METHOD OF FORMING ENERGY SUBTRACTION IMAGES

[75] Inventor: Hideya Takeo, Kanagawa-ken, Japan

[73] Assignee: Fuji Photo Film Co., Ltd., Kanagawa-ken, Japan

[21] Appl. No.: 09/229,687

[22] Filed: Jan. 13, 1999

[30] Foreign Application Priority Data

Jan. 13, 1998 [JP] Japan .................................. 10-005027
Jun. 9, 1998 [JP] Japan .................................. 10-160921

[51] Int. Cl.[7] .................................................. G01N 23/04
[52] U.S. Cl. .......................... 378/98.12; 378/62; 378/98.9; 378/98.11
[58] Field of Search .......................... 378/62, 98.9, 98.11, 378/98.12; 382/130

[56] References Cited

U.S. PATENT DOCUMENTS

| | | | |
|---|---|---|---|
| 4,564,861 | 1/1986 | Hishinuma et al. | 250/582 |
| 4,710,875 | 12/1987 | Nakajima et al. | 378/162 |
| 4,816,681 | 3/1989 | Shimura | 250/587 |
| 4,855,598 | 8/1989 | Ohgoda et al. | 250/582 |
| 4,896,037 | 1/1990 | Shimura et al. | 250/583 |
| 5,020,085 | 5/1991 | Kawara et al. | 378/98.11 |
| 5,048,110 | 9/1991 | Nakajima | 382/130 |
| 5,049,746 | 9/1991 | Ito | 250/583 |
| 5,210,415 | 5/1993 | Ito | 250/584 |
| 5,291,403 | 3/1994 | Ito | 250/587 |
| 5,301,107 | 4/1994 | Shimura | 378/51 |
| 5,402,338 | 3/1995 | Ito | 600/407 |
| 5,485,371 | 1/1996 | Ito et al. | 378/20 |
| 5,535,289 | 7/1996 | Ito | 382/130 |

FOREIGN PATENT DOCUMENTS 3-285475   12/1991   Japan .......................... H04N 5/325

*Primary Examiner*—David V. Bruce
*Assistant Examiner*—Allen C Ho
*Attorney, Agent, or Firm*—Sughrue, Mion, Zinn, Macpeak & Seas, PLLC

[57] ABSTRACT

In a method of forming an energy subtraction image, an S value (a sensitivity value) corresponding to a dose of radiation delivered in an operation for recording a radiation image is calculated from an image signal, which is obtained by reading out the radiation image. In cases where the S value is large, i.e. in cases where the dose of radiation is small, since the level of noise is high, the number of repetitions of noise reducing processes is set to be large, or the degree of a smoothing process is set to be high. In cases where the S value is small, i.e. in cases where the dose of radiation is large, since the level of noise is low, the number of repetitions of noise reducing processes is set to be small, or the degree of a smoothing process is set to be low. An energy subtraction image having good image quality is thereby obtained.

7 Claims, 11 Drawing Sheets

F I G. 1
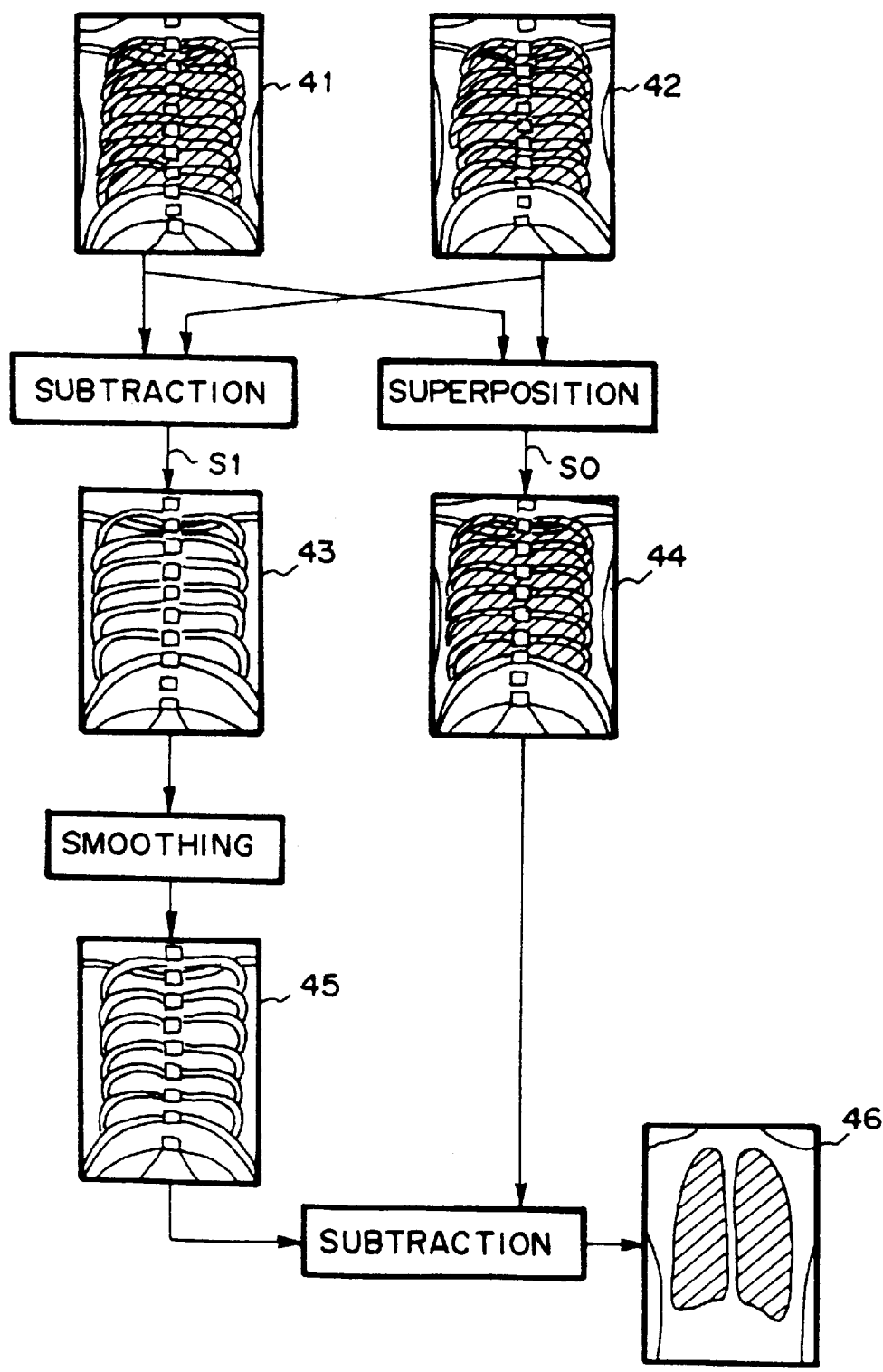

F I G . 2
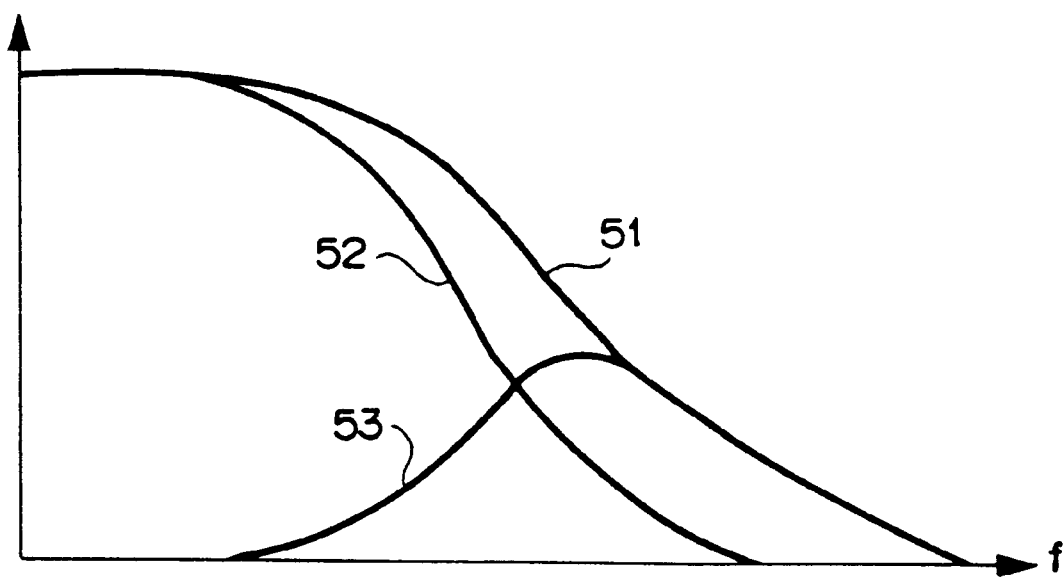

F I G. 10
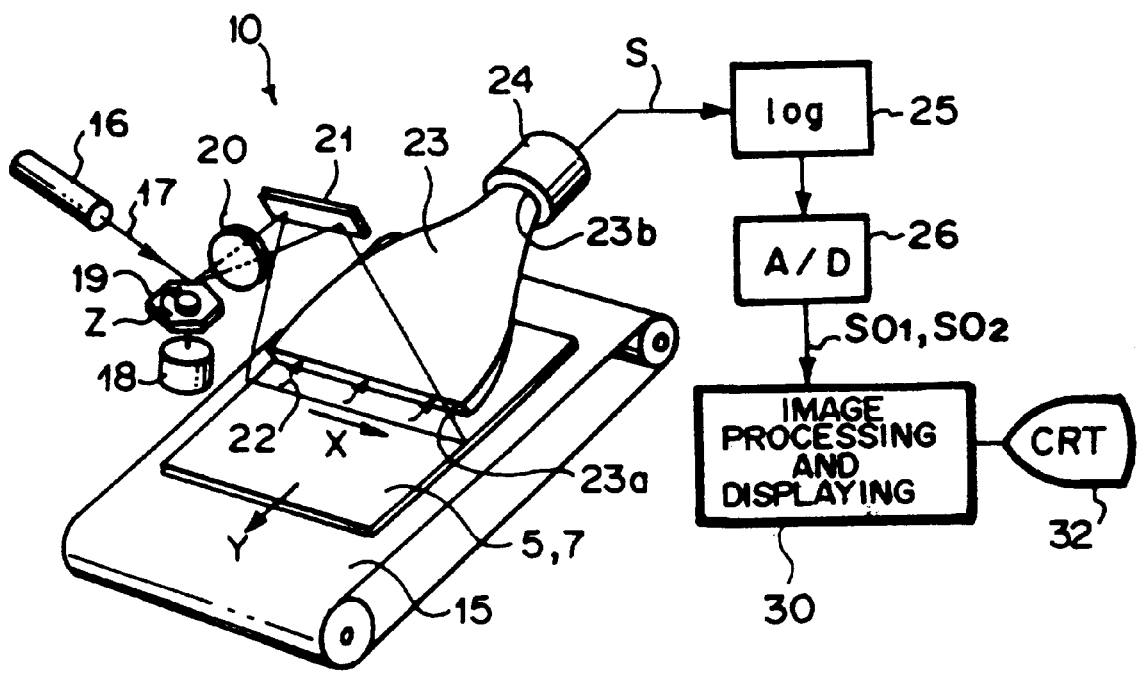

FIG.11

| S VALUE | N | M |
|---|---|---|
| ~50 | 1 | 1 |
| 50~100 | 2 | 1 |
| 100~200 | 2 | 2 |
| 200~300 | 3 | 2 |
| 300~ | 3 | 3 |

FIG.12

| S VALUE | |
|---|---|
| 0 ~ 50 | NO SMOOTHING PROCESS IS CARRIED OUT |
| 50 ~100 | THE SECOND AND THIRD SMOOTHING PROCESSES ARE NOT CARRIED OUT |
| 100~200 | THE THIRD SMOOTHING PROCESS IS NOT CARRIED OUT |
| 200~ | ALL OF THE THREE SMOOTHING PROCESSES ARE CARRIED OUT |

METHOD OF FORMING ENERGY SUBTRACTION IMAGES

BACKGROUND OF THE INVENTION

1. Field of the Invention

This invention relates to a method of forming an energy subtraction image wherein, from a plurality of radiation images, an energy subtraction image is formed which includes little noise and which has good image quality and can serve as an effective tool in, particularly, the efficient and accurate diagnosis of an illness.

2. Description of the Prior Art

Techniques for reading out a recorded radiation image in order to obtain an image signal, carrying out appropriate image processing on the image signal, and then reproducing a visible image by use of the processed image signal have heretofore been known in various fields. For example, an X-ray image is recorded on an X-ray film having a small gamma value chosen according to the type of image processing to be carried out, and the X-ray image is read out from the X-ray film and converted into an electric signal (i.e., an image signal). The image signal is processed and then used for reproducing the X-ray image as a visible image on a photocopy, or the like. In this manner, a visible image having good image quality with high contrast, high sharpness, high graininess, or the like, can be reproduced.

Further, it has been proposed to use stimulable phosphors in radiation image recording and reproducing systems. Specifically, a radiation image of an object, such as a human body, is recorded on a sheet provided with a layer of the stimulable phosphor (hereinafter referred to as a stimulable phosphor sheet). The stimulable phosphor sheet, on which the radiation image has been stored, is then exposed to stimulating rays, such as a laser beam, which cause it to emit light in proportion to the amount of energy stored thereon during its exposure to the radiation. The light emitted by the stimulable phosphor sheet, upon stimulation thereof, is detected and converted into an electric image signal. The image signal is then processed and used for the reproduction of the radiation image of the object as a visible image on a recording material.

In the radiation image recording and reproducing systems wherein recording media, such as X-ray film or stimulable phosphor sheets are used, subtraction processing techniques for radiation images are often carried out on image signals detected from a plurality of radiation images of an object, which have been recorded on the recording media.

With the subtraction processing techniques for radiation images, an image is obtained which corresponds to a difference between a plurality of radiation images of an object recorded under different conditions. Specifically, a plurality of the radiation images recorded under different conditions are read out at predetermined sampling intervals, and a plurality of image signals thus detected are converted into digital image signals which represent the radiation images. The image signal components of the digital image signals, which components represent the image information recorded at corresponding sampling points in the radiation images, are then subtracted from each other. A difference signal is thereby obtained which represents the image of a specific structure or part of the object represented by the radiation images.

Basically, subtraction processing is carried out with either the so-called temporal (time difference) subtraction processing method or the so-called energy subtraction processing method. In the former method, in order for the image of a specific structure (for example, a blood vessel) of an object to be extracted from the image of the whole object, the image signal representing a radiation image obtained without injection of contrast media is subtracted from the image signal representing a radiation image in which the image of the specific structure (for example, a blood vessel) of the object is enhanced by the injection of contrast media. In the latter method, such characteristics are utilized that a specific structure of an object exhibits different levels of radiation absorptivity with respect to radiation with different energy distributions. Specifically, an object is exposed to several kinds of radiation with different energy distributions. Alternatively, the energy distribution of the radiation carrying image information of an object, is changed after it has been irradiated onto one of a plurality of radiation image recording media, after which the radiation impinges upon the second radiation image recording medium. In this manner, a plurality of radiation images are obtained in which different images of a specific structure are embedded. Thereafter, the image signals representing the plurality of the radiation images are weighted appropriately and subjected to a subtraction process in order to extract the image of the specific structure. The applicant proposed novel energy subtraction processing methods using stimulable phosphor sheets in, for example, U.S. Pat. Nos. 4,855,598 and 4,896,037.

A plurality of radiation images, which are subjected to energy subtraction processing, will herein be referred to as the "original images." An image signal representing a subtraction image is obtained by subtracting the image signals representing the original images from each other. Therefore, the image signal representing the subtraction image has a lower signal-to-noise ratio (S/N ratio) than the image signals representing the original images. As a result, the problems occur in that the image quality of the subtraction image becomes worse than the image quality of the original images.

By way of example, energy subtraction processing is often carried out in the manner described below. Specifically, an object, such as the chest of a human body, which is constituted of soft tissues and bones, is exposed to several kinds of radiation with different energy levels, and a plurality of radiation images of the object are thereby obtained. The plurality of the radiation images are read out, and a plurality of image signals representing the radiation images are generated. Energy subtraction processing is then carried out on the plurality of the image signals. From the energy subtraction processing, a soft tissue image signal is obtained which represents a soft tissue image primarily composed of patterns of the soft tissues of the object. Alternatively, a bone image signal is obtained which represents a bone image primarily composed of patterns of the bones of the object. Thereafter, the soft tissue image is reproduced as a visible image from the soft tissue image signal, or the bone image is reproduced as a visible image from the bone image signal. In the soft tissue image, the patterns of the bones have been erased. Therefore, patterns, which were behind the bone patterns or were rendered imperceptible by the bone patterns in the original images, become more perceptible in the soft tissue image than in the original images. Also, in the bone image, the patterns of the soft tissues have been erased. Therefore, patterns, which were behind the soft tissue patterns or were rendered imperceptible by the soft tissue patterns in the original images, become more perceptible in the bone image than in the original images. Accordingly, a subtraction image can be obtained which is well matched to the purposes of diagnosis. However, because the soft tissue image and the bone image are obtained from the subtraction processing, the problems occur in that noise components have been emphasized in the soft tissue image and the bone image than in the original images. From this point of view, the image quality of the soft tissue image and the bone image could not heretofore been kept good.

Accordingly, in Japanese Unexamined Patent Publication No. 3(1991)-285475, the applicant proposed a method of forming an energy subtraction image wherein a subtraction image, in which noise has been reduced to approximately the same level as that in the original image, is formed. The proposed method comprises the steps of: (i) forming a first image signal, which represents a first image primarily composed of patterns of first tissues of an object, from a plurality of original image signals subjected to energy subtraction processing, (ii) forming a first smoothed image signal by processing the first image signal, the first smoothed image signal representing a first smoothed image in which noise components of the first image have been reduced or eliminated, and (iii) forming a second image signal by subtracting the first smoothed image signal from an original image signal, the second image signal representing a second image primarily composed of patterns of second tissues of the object. With the proposed method, processing may then be carried out on the second image signal, and a new first image signal, which represents a new first image primarily composed of the patterns of the first tissues of the object and in which noise components have been reduced even further, may thereby be formed. Such processes may be repeated, and an energy subtraction image, in which noise has been reduced and which has good image quality, may thereby be formed.

With the method proposed in Japanese Unexamined Patent Publication No. 3(1991)-285475, an energy subtraction image, in which noise has been reduced, can be obtained. However, in cases where little noise is contained in the original image signals, if the processes described above are carried out repeatedly, though the noise level will become very low, an image, which gives an unnatural feeling, such as a feeling of a picturized image, and is unsightly, will be obtained.

SUMMARY OF THE INVENTION

The primary object of the present invention is to provide a method of forming an energy subtraction image, wherein an energy subtraction image is formed, in which noise has been reduced to approximately the same level as that in an original image before being subjected to energy subtraction processing, which gives a natural feeling, and which has good image quality and can serve as an effective tool in, particularly, the efficient and accurate diagnosis of an illness.

Another object of the present invention is to provide a method of forming an energy subtraction image, wherein an energy subtraction image is formed which has image quality enhanced even further.

The present invention provides a first method of forming an energy subtraction image, comprising the steps of:
i) after a plurality of radiation images of an object are formed with a plurality of kinds of radiation having different energy distributions, the object being constituted of a plurality of tissues exhibiting different levels of radiation absorptivity, and a plurality of original image signals, each of which represents one of the radiation images, are then detected, carrying out a first process for obtaining a first image signal, which represents a first image primarily composed of patterns of first tissues of the object, from the plurality of the original image signals, ii) thereafter carrying out a second process, which comprises the steps of:
   a) obtaining a first smoothed image signal by processing the first image signal, the first smoothed image signal representing a first smoothed image in which noise components of the first image have been reduced, and
   b) obtaining a second image signal by subtracting the first smoothed image signal from an original image signal, the second image signal representing a second image primarily composed of patterns of second tissues of the object, iii) thereafter carrying out a third process, which comprises the steps of:
   a) obtaining a second smoothed image signal by processing the second image signal, the second smoothed image signal representing a second smoothed image in which noise components of the second image have been reduced, and
   b) obtaining a new first image signal by subtracting the second smoothed image signal from an original image signal, the new first image signal representing a new first image primarily composed of the patterns of the first tissues of the object, and iv) thereafter repeating the following a predetermined number of times:
   a) a new second process for obtaining a new second image signal by carrying out the second process in which the new first image signal having been obtained from the third process is taken as the first image signal in the second process, the new second image signal formed by the new second process representing a new second image primarily composed of the patterns of the second tissues of the object, and
   b) a new third process for obtaining a new first image signal by carrying out the third process in which the new second image signal is taken as the second image signal in the third process, the new first image signal obtained from the new third process representing a new first image primarily composed of the patterns of the first tissues of the object, wherein the improvement comprises determining the number of repetitions of the new second process and the new third process in accordance with a dose of radiation at the time, at which the original image signals were obtained.

By the application of the first method of forming an energy subtraction image in accordance with the present invention, a new second image signal can be obtained ultimately which represents a new second image primarily composed of the patterns of the second tissues of the object. Specifically, the present invention also provides a second method of forming an energy subtraction image, comprising the steps of:
i) carrying out the processes in the first method of forming an energy subtraction image in accordance with the present invention, and
ii) thereafter obtaining a new second image signal by carrying out the second process or the new second process in which the new first image signal having been obtained from the third process or the new third process is taken as the first image signal in the second process or the new second process, the new second image signal thus most recently obtained representing a new second image primarily composed of the patterns of the second tissues of the object.

The terms "first image" and "second image" (or the terms "new first image" and "new second image") as used herein mean two images, which have been obtained from energy subtraction processing and in which the patterns of different tissues of a single object have been emphasized or only such patterns are illustrated. The first image and the second image (or the new first image and the new second image) are not limited to specific images. By way of example, the first image and the second image (or the new first image and the new second image) may be a soft tissue image and a bone image. Alternatively, in cases where the object is a mamma of a human body, the first image and the second image (or the new first image and the new second image) may be an image, in which the patterns of mammary glands have been emphasized, and an image, in which the pattern of a malignant tumor has been emphasized.

Also, the term "repeating a predetermined number of times" as used herein means that the number of repetitions is one time, several times, or null time.

Further, the term "dose of radiation" as used herein means the actual dose of radiation irradiated when the radiation image of the object was recorded, or a central value of normalization (i.e., the so-called "S value"), which is an index value representing the read-out sensitivity in the operation for reading out the image having been recorded on a stimulable phosphor sheet or X-ray film.

In the above-described first and second methods of forming an energy subtraction image and also in the below-described various other methods according to the present invention, including those defined in claims, the expression of "with a plurality of kinds of radiation having different energy distributions" does not necessarily mean a plurality of separate radiations but includes a plurality of kinds of radiations originated from a single radiation wherein, for example, one is a direct radiation from a radiation source, and the other is a radiation from the same radiation source, which has passed through a recording medium (e.g., a stimulable phosphor sheet) and/or a filter, or the like, and the low energy components of which have been filtered out. Therefore, the plurality of the radiation images can be formed one after another by using different radiations having different energy distributions. Alternatively, the plurality of the radiation images can be formed simultaneously by using a single radiation and placing a plurality of recording media (e.g., stimulable phosphor sheets) one upon another with or without a filter interposed therebetween. When the filter is not used, the stimulable phosphor sheet located closer to the radiation source serves as a filter for filtering out the low energy components of the radiation.

The present invention further provides a third method of forming an energy subtraction image, comprising the steps of:

i) after a plurality of radiation images of an object are formed with a plurality of kinds of radiation having different energy distributions, the object being constituted of a plurality of tissues exhibiting different levels of radiation absorptivity with respect to the plurality of kinds of radiation, and a plurality of original image signals, each of which represents one of the radiation images, are then detected, obtaining a first image signal, which represents a first image primarily composed of patterns of first tissues of the object, from the plurality of the original image signals, ii) obtaining a first smoothed image signal by carrying out a smoothing process on the first image signal, the first smoothed image signal representing a first smoothed image in which noise components of the first image have been reduced or eliminated, and iii) obtaining a second image signal by subtracting the first smoothed image signal from an original image signal, the second image signal representing a second image primarily composed of patterns of second tissues of the object, wherein the improvement comprises setting the degree of the smoothing process, which is carried out on the first image signal, to be low as a dose of radiation at the time, at which the original image signals were obtained, becomes large.

In order for the degree of the smoothing process to be set to be low, for example, the size of a filter employed in the smoothing process may be set to be small, or the kind of the filter may be altered to a median filter or a filter, in which the degree of weighting of a center point is high. The term "setting a degree of smoothing process to be low" as used herein also embraces the cases wherein the smoothing process is not carried out. In the third method of forming an energy subtraction image in accordance with the present invention (and those that follow), in cases where the dose of radiation is small, the degree of the smoothing process is set to be large. For such purposes, for example, the size of the filter may be set to be large.

The third method of forming an energy subtraction image in accordance with the present invention may be embodied in various, substantially identical manners. For example, each of the steps of the third method of forming an energy subtraction image in accordance with the present invention may be divided even further into a plurality of steps. Alternatively, the operations may be carried out in different orders. Thus the third method of forming an energy subtraction image in accordance with the present invention includes such various, substantially identical methods.

The present invention still further provides a fourth method of forming an energy subtraction image, comprising the steps of:

i) after a plurality of radiation images of an object are formed with a plurality of kinds of radiation having different energy distributions, the object being constituted of a plurality of tissues exhibiting different levels of radiation absorptivity with respect to the plurality of kinds of radiation, and a plurality of original image signals, each of which represents one of the radiation images, are then detected, carrying out a first process for obtaining a first image signal, which represents a first image primarily composed of patterns of first tissues of the object, from the plurality of the original image signals, ii) thereafter carrying out a second process, which comprises the steps of:

a) obtaining a first smoothed image signal by processing the first image signal, the first smoothed image signal representing a first smoothed image in which noise components of the first image have been reduced, and b) obtaining a second image signal by subtracting the first smoothed image signal from an original image signal, the second image signal representing a second image primarily composed of patterns of second tissues of the object, and iii) thereafter carrying out a third process, which comprises the steps of:
  a) obtaining a second smoothed image signal by carrying out a smoothing process on the second image signal, the second smoothed image signal representing a second smoothed image in which noise components of the second image have been reduced, and
  b) obtaining a new first image signal by subtracting the second smoothed image signal from an original image signal, the new first image signal representing a new first image primarily composed of the patterns of the first tissues of the object,
wherein the improvement comprises setting the degree of the smoothing process, which is carried out on the first image signal, and the degree of the smoothing process, which is carried out on the second image signal, to be low as a dose of radiation at the time, at which the original image signals were obtained, becomes large.

An image having better image quality can be obtained by repeating the second and third processes in the fourth method of forming an energy subtraction image in accordance with the present invention. Specifically, the present invention also provides a fifth method of forming an energy subtraction image comprising the steps of:
  i) carrying out the processes in the fourth method of forming an energy subtraction image in accordance with the present invention, and
  ii) thereafter repeating the following a predetermined number of times:
    a) a new second process for obtaining a new second image signal by carrying out the second process in which the new first image signal having been obtained from the third process is taken as the first image signal in the second process, the new second image signal formed by the new second process representing a new second image primarily composed of the patterns of the second tissues of the object, and
    b) a new third process for obtaining a new first image signal by carrying out the third process in which the new second image signal is taken as the second image signal in the third process, the new first image signal obtained from the new third process representing a new first image primarily composed of the patterns of the first tissues of the object.

Also, an image having image quality enhanced even further can be obtained by altering the number of repetitions of the new second process and the new third process, which are carried out in the aforesaid fifth method of forming an energy subtraction image. Specifically, the present invention further provides a sixth method of forming an energy subtraction image wherein the number of repetitions of the new second process and the new third process is determined in accordance with a dose of radiation at the time, at which the original image signals were obtained.

By the application of one of the aforesaid fourth, fifth, and sixth methods of forming an energy subtraction image in accordance with the present invention, a new second image signal can be obtained ultimately which represents a new second image primarily composed of the patterns of the second tissues of the object. Specifically, the present invention still further provides a seventh method of forming an energy subtraction image, comprising the steps of:
  i) carrying out the processes in one of the aforesaid fourth, fifth, and sixth methods of forming an energy subtraction image in accordance with the present invention, and
  ii) thereafter obtaining a new second image signal by carrying out the second process or the new second process in which the new first image signal having been obtained from the third process or the new third process is taken as the first image signal in the second process or the new second process, the new second image signal thus most recently obtained representing a new second image primarily composed of the patterns of the second tissues of the object.

The methods of forming an energy subtraction image in accordance with the present invention are based upon the findings in that the level of noise contained in a radiation image is low in cases where the dose of radiation at the time, at which the radiation image of an object was recorded, is large, and in that the level of noise contained in the radiation image is high in cases where the dose of radiation is small.

Specifically, with the first and second methods of forming an energy subtraction image in accordance with the present invention, the number of repetitions of the noise reducing processes, which are carried out in the method of forming an energy subtraction image proposed in Japanese Unexamined Patent Publication No. 3(1991)-285475, is determined in accordance with the dose of radiation at the time, at which the original image signals were obtained. Therefore, in cases where the dose of radiation is large, the number of repetitions can be set to be small. Also, in cases where the dose of radiation is small, the number of repetitions can be set to be large. As a result, in cases where the level of noise contained in the original image signals is low, the first and second images, in which an appropriate level of noise remains and which give a natural feeling, can be obtained. Also, in cases where the level of noise contained in the original image signals is high, the first and second images, in which noise has been reduced and which have good image quality and can serve as an effective tool in, particularly, the efficient and accurate diagnosis of an illness, can be obtained.

With the third and fourth methods of forming an energy subtraction image in accordance with the present invention, the degrees of smoothing processes for obtaining the first and second smoothed image signals, which processes are carried out in the method of forming an energy subtraction image proposed in Japanese Unexamined Patent Publication No. 3(1991)-285475, are set to be low as the dose of radiation at the time, at which the original image signals were obtained, becomes large. In cases where the dose of radiation is large, since the level of noise contained in the original image signals is low, a sharper image can be reproduced when the degree of each smoothing process is set to be low, such that the image subjected to the smoothing process may not be blurred, than when the image subjected to the smoothing process is blurred with the smoothing process. Therefore, with the third and fourth methods of forming an energy subtraction image in accordance with the present invention, in cases where the dose of radiation is large, i.e. in cases where the level of noise is low, the degree of blurring of the image with the smoothing process is set to be low. Accordingly, the first and second images, which have not much been blurred and have good image quality and can serve as an effective tool in, particularly, the efficient and accurate diagnosis of an illness, can be obtained.

With the fifth method of forming an energy subtraction image in accordance with the present invention, the steps of the fourth method of forming an energy subtraction image in accordance with the present invention are carried out repeatedly such that more noise components can be reduced. The respective noise reducing processes can be allotted with appropriate modes of processing. Therefore, an image can be obtained in which noise components have been reduced even further.

With the sixth method of forming an energy subtraction image in accordance with the present invention, the number of repetitions of the noise reducing processes, which are carried out in the aforesaid fifth method of forming an energy subtraction image in accordance with the present invention, is determined in accordance with the dose of radiation at the time, at which the original image signals were obtained. Therefore, in cases where the dose of radiation is large, the number of repetitions can be set to be small. Also, in cases where the dose of radiation is small, the number of repetitions can be set to be large. As a result, in cases where the level of noise contained in the original image signals is low, the first and second images, in which an appropriate level of noise remains and which give a natural feeling, can be obtained. Also, in cases where the level of noise contained in the original image signals is high, the first and second images, in which noise has been reduced and which have good image quality and can serve as an effective tool in, particularly, the efficient and accurate diagnosis of an illness, can be obtained.

With the seventh method of forming an energy subtraction image in accordance with the present invention, after the steps of the aforesaid fourth, fifth, or sixth method of forming an energy subtraction image in accordance with the present invention have been carried out, a noise reducing process is carried out on the new first image signal, which has been obtained from the fourth, fifth, or sixth method of forming an energy subtraction image. In this manner, a new first smoothed image signal is obtained. Thereafter, the new first smoothed image signal is subtracted from an original image signal. Accordingly, the new second image can be obtained in which noise components have been reduced.

BRIEF DESCRIPTION OF THE DRAWINGS

FIG. 1 is a flow chart showing the fundamental processing, which is carried out in an image processing and displaying apparatus, FIG. 2 is a graph showing spatial frequency spectra of a bone image and an image obtained by processing the bone image signal representing the bone image, FIG. 10 is a perspective view showing an X-ray image read-out apparatus and an image processing and displaying apparatus, in which the method of forming an energy subtraction image in accordance with the present invention may be employed, FIG. 11 is a table showing how the number of repetitions of processes is set, and FIG. 12 is a table showing how the degree of a smoothing process is set in accordance with an S value.

DESCRIPTION OF THE PREFERRED EMBODIMENTS

The present invention will hereinbelow be described in further detail with reference to the accompanying drawings. In the embodiments described below, stimulable phosphor sheets are utilized as the recording media.

Figure 9:
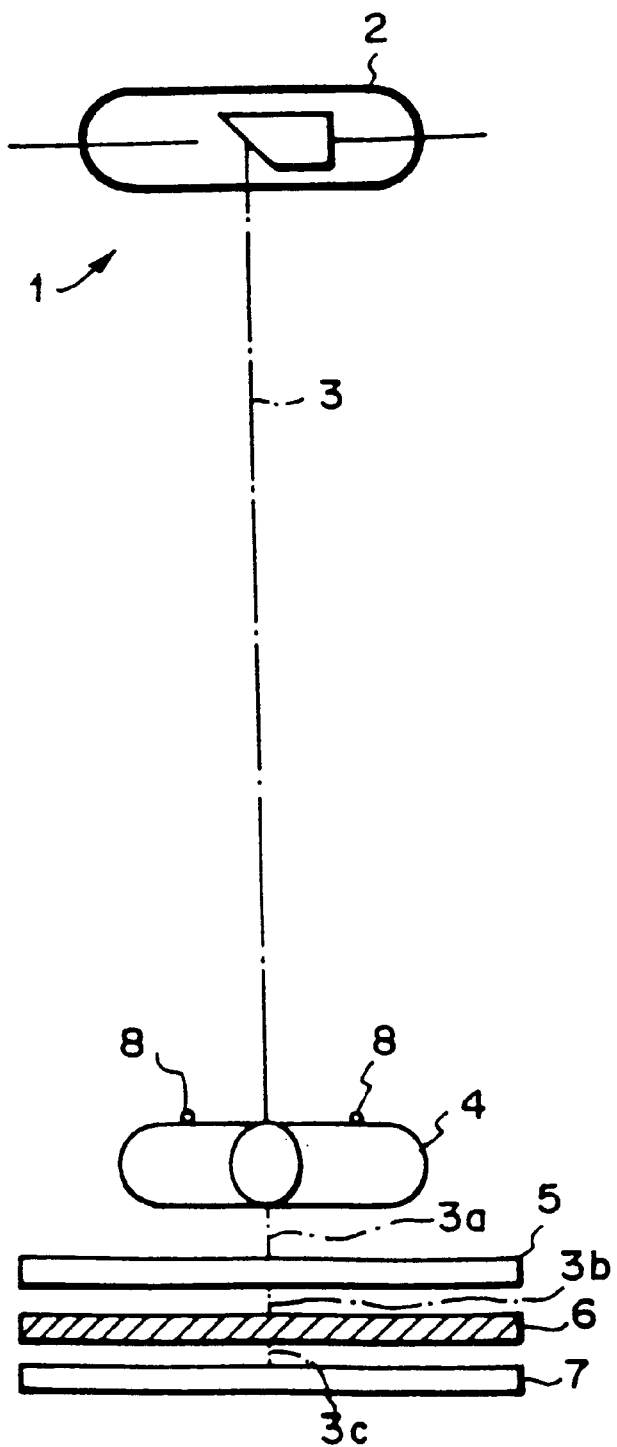
FIG. 9 is a schematic view showing an X-ray image recording apparatus.

FIG. 9 is a schematic view showing an X-ray image recording apparatus 1.

With reference to FIG. 9, X-rays 3 are produced by an X-ray tube 2 of the X-ray image recording apparatus 1 and irradiated to an object 4 (in this example, the chest of a human body). X-rays 3a, which have passed through the object 4, impinge upon a first stimulable phosphor sheet 5, and energy from the comparatively low energy components of the X-rays 3a is stored on the first stimulable phosphor sheet 5. In this manner, an X-ray image of the object 4 is stored on the first stimulable phosphor sheet 5. X-rays 3b, which have passed through the first stimulable phosphor sheet 5, then pass through a filter 6 for filtering out the low energy components of the X-rays. X-rays 3c, which have passed through the filter 6 and are composed of the high energy components, impinge upon a second stimulable phosphor sheet 7. In this manner, an X-ray image of the object 4 is stored on the second stimulable phosphor sheet 7. During the image recording operation, marks 8, 8 are placed on the object 4. The images of the marks 8, 8 are utilized in the course of adjusting the positions of the two X-ray images so that the two X-ray images coincide with each other.

In the X-ray image recording apparatus 1, the X-ray images are stored on the first stimulable phosphor sheet 5 and the second stimulable phosphor sheet 7 with a single, simultaneous recording operation. Alternatively, the two X-ray images may be recorded one after the other with two independent recording operations.

FIG. 10 is a perspective view showing an X-ray image read-out apparatus 10 and an image processing and displaying apparatus 30, in which the method of forming an energy subtraction image in accordance with the present invention may be employed.

After the first X-ray image and the second X-ray image have been stored respectively on the first stimulable phosphor sheet 5 and the second stimulable phosphor sheet 7 in the X-ray image recording apparatus 1 shown in FIG. 9, the first stimulable phosphor sheet 5 and the second stimulable phosphor sheet 7 are placed one after the other at a predetermined position in the X-ray image read-out apparatus 10 shown in FIG. 10. How the first X-ray image is read out from the first stimulable phosphor sheet 5 will be described hereinbelow.

With reference to FIG. 10, the first stimulable phosphor sheet 5 is conveyed in a sub-scanning direction indicated by the arrow Y by a sheet conveyance means 15, which is constituted of an endless belt, or the like, and which is operated by an operating means (not shown). A laser beam 17, which serves as stimulating rays, is produced by a laser beam source 16. The laser beam 17 is reflected and deflected by a rotating polygon mirror 19, which is being quickly rotated by a motor 18 in the direction indicated by the arrow Z. The laser beam 17 then passes through a converging lens 20, which may be constituted of an fθ lens, or the like. The direction of the optical path of the laser beam 17 is then changed by a mirror 21, and the laser beam 17 is caused to impinge upon the first stimulable phosphor sheet 5 and scan it in a main scanning direction indicated by the arrow X. The main scanning direction is approximately normal to the sub-scanning direction indicated by the arrow Y. When the first stimulable phosphor sheet 5 is exposed to the laser beam 17, the exposed portion of the first stimulable phosphor sheet 5 emits light 22 in an amount proportional to the amount of energy stored thereon during its exposure to the X-rays. The emitted light 22 is guided by a light guide member 23, and photoelectrically detected by a photomultiplier 24. The light guide member 23 is made from a light guiding material, such as an acrylic plate. The light guide member 23 has a linear light input face 23a, positioned to extend along the main scanning line on the first stimulable phosphor sheet 5, and a ring-shaped light output face 23b, positioned so that it is in close contact with a light receiving face of the photomultiplier 24. The emitted light 22, which has entered the light guide member 23 from its light input face 23a, is guided through repeated total reflection inside of the light guide member 23, emanates from the light output face 23b, and is received by the photomultiplier 24. In this manner, the amount of the emitted light 22, which amount represents the first X-ray image stored on the first stimulable phosphor sheet 5, is converted into an electric signal by the photomultiplier 24.

An analog signal S generated by the photomultiplier 24 is logarithmically amplified by a logarithmic amplifier 25, and fed into an analog-to-digital converter 26. The analog-to-digital converter 26 samples the analog signal S, and the sampled signal is converted into a digital image signal SO. The image signal SO thus obtained represents the first X-ray image, which was stored on the first stimulable phosphor sheet 5, and will hereafter be referred to as the first image signal $SO_1$ (the first original image signal). The first image signal $SO_1$ is stored in an internal memory of the image processing and displaying apparatus 30.

The image processing and displaying apparatus 30 is provided with a keyboard (not shown), from which various instructions are entered, and a CRT display device 32, which displays auxiliary information for instructions and a visible image represented by an image signal.

Thereafter, in the same manner as that described above, a second image signal $SO_2$ (a second original image signal) is obtained which represents the second X-ray image stored on the second stimulable phosphor sheet 7. The second image signal $SO_2$ is stored in the internal memory of the image processing and displaying apparatus 30.

When the first image signal $SO_1$ and the second image signal $SO_2$ are thus detected, an S value, which represents the sensitivity of the photomultiplier 24, is calculated from the obtained image signals $SO_1$ and $SO_2$. The S value is obtained by calculating the mean picture element values of the image signals $SO_1$ and $SO_2$ and normalizing the picture element values.

FIG. 1 is a flow chart showing the fundamental processing, which is carried out in the image processing and displaying apparatus 30. The processing is carried out on the first image signal $SO_1$ representing the first X-ray image and the second image signal $SO_2$ representing the second X-ray image, which signals are stored in the internal memory of the image processing and displaying apparatus 30.

The first image signal $SO_1$ and the second image signal $SO_2$, which are stored in the internal memory of the image processing and displaying apparatus 30, represent a first X-ray image 41 and a second X-ray image 42 shown in FIG. 1. The first X-ray image 41 has been recorded with the comparatively low energy components of the X-rays. The second X-ray image 42 has been recorded with the comparatively high energy components of the X-rays. Both of the first X-ray image 41 and the second X-ray image 42 are original images composed of patterns of soft tissues and bones. The levels of image density of the soft tissue patterns and the bone patterns are different between the first X-ray image 41 and the second X-ray image 42.

The first image signal $SO_1$ and the second image signal $SO_2$ are read from the internal memory of the image processing and displaying apparatus 30 shown in FIG. 10. Position adjustment processing is then carried out on the first image signal $SO_1$ and the second image signal $SO_2$ such that the positions of the first X-ray image 41 represented by the first image signal $SO_1$ and the second X-ray image 42 represented by the second image signal $SO_2$ may coincide with each other. For this purpose, a method disclosed in, for example, U.S. Pat. No. 4,710,875 may be employed. With the position adjustment processing, one of the two X-ray images is linearly moved or rotated with respect to the other X-ray image until the images of the marks 8, 8 in one X-ray image, which marks are shown in FIG. 9, overlap the images of the marks 8, 8 in the other X-ray image.

Thereafter, a subtraction process is carried out on the first image signal $SO_1$ and the second image signal $SO_2$.

Specifically, X-ray absorption coefficients $\mu$ are classified into the following:

$\mu_L^T$: Absorption coefficient of soft tissues with respect to the low energy components of X-rays.

$\mu_H^T$: Absorption coefficient of soft tissues with respect to the high energy components of X-rays.

$\mu_L^B$: Absorption coefficient of bones with respect to the low energy components of X-rays.

$\mu_H^B$: Absorption coefficient of bones with respect to the high energy components of X-rays.

The first image signal $SO_1$ and the second image signal $SO_2$ are weighted, and the image signal components of the weighted image signals are subtracted from each other, which image signal components represent the image information stored at corresponding picture elements in the two X-ray images. Thus a bone image signal S1 is obtained, which can be expressed as $$S1 = SO_1 - (\mu_L^T/\mu_H^T) \cdot SO_2 + C \tag{1}$$

where C represents a bias component. The bone image signal S1 represents a bone image 43 shown in FIG. 1, which image is composed of the bone patterns.

The first image signal $SO_1$ and the second image signal $SO_2$ may be weighted in a different way, and the image signal components of the weighted image signals may be subtracted from each other which represent the image information stored at corresponding picture elements in the two X-ray images. In this manner, a soft tissue image signal S2 can be obtained, which is expressed as $$S2 = (\mu_L^B/\mu_H^B)SO_2 - SO_1 + C' \tag{2}$$

where C' represents a bias component. The soft tissue image signal S2 represents a soft tissue image composed of the soft tissue patterns. However, in this embodiment, the operations for forming the soft tissue image signal S2 need not be carried out.

Also, the image signal components of the first image signal $SO_1$ and the second image signal $SO_2$ are added to each other, which image signal components represent the image information stored at corresponding picture elements in the two X-ray images. In this manner, a superposition image signal SO is obtained, which can be expressed as $$SO=(SO_1+SO_2)/2 \qquad (3)$$

The superposition image signal SO represents a superposition image 44 shown in FIG. 1, which results from the superposition of the first X-ray image 41 and the second X-ray image 42 upon each other. The super position image 44 can also be referred to as one kind of original image, which is composed of the soft tissue patterns and the bone patterns. In the method of forming an energy subtraction image in accordance with the present invention, the first X-ray image 41 or the second X-ray image 42 may be utilized in lieu of the superposition image 44. However, the superposition image 44 should preferably be utilized. This is because the superposition image 44, which is obtained from the superposition of the first X-ray image 41 and the second X-ray image 42 upon each other, includes less noise components than the first X-ray image 41 and the second X-ray image 42, and therefore is advantageous for the subsequent processes.

Thereafter, the bone image signal S1 is processed such that noise components contained in the bone image 43 may be eliminated.

FIG. 2 is a graph showing spectra of a bone image and an image, which is obtained by processing the bone image signal representing the bone image, with respect to the spatial frequency, f.

In FIG. 2, curve 51 indicates the spectrum of the bone image 43, and curve 53 indicates the spectrum of noise components included in the bone image 43.

Firstly, a smoothing process is carried out on the bone image signal S1. As the smoothing process, one of various processes may be employed. For example, a simple averaging process (unsharp mask processing) may be employed wherein an unsharp mask having a predetermined region is utilized, and the mean value of the values of the image signal components of an image signal, which represent the picture elements belonging to the predetermined region having a predetermined picture element in the middle, is calculated and employed as the value of the image signal component representing the predetermined picture element. Alternatively, a median filter process may be employed wherein the median value of the values of the image signal components of an image signal, which represent the picture elements belonging to a predetermined region having a predetermined picture element in the middle, is calculated and employed as the value of the image signal component representing the predetermined picture element. As another alternative, an edge keeping filter (V-filter) process may be employed wherein a predetermined region having a predetermined picture element in the middle is divided into a plurality of small regions, and the variance of the values of the image signal components corresponding to each small region is calculated. A small region associated with the smallest variance is then found, and the mean value of the values of the image signal components corresponding to the small region associated with the smallest variance is employed as the value of the image signal component representing the predetermined picture element. As a further alternative, a process may be employed wherein Fourier transformation is carried out on an image signal, the signal obtained from the Fourier transformation is subjected to an operation for removing high spatial frequency components corresponding to noise components, and thereafter inverse Fourier transformation is carried out.

However, the simple averaging process (unsharp mask processing) has the drawbacks in that edges in the image become unsharp. The median filter process has the drawbacks in that, because picture elements are interchanged, contour line-like artifacts often occur. The edge keeping filter process has the drawbacks in that honeycomb-like artifacts often occur. The Fourier transformation process has the drawbacks in that a long time is taken for operations to be carried out.

Therefore, in this embodiment, as will be described below, a smoothing process is carried out in which a filter adaptive to a histogram is utilized. With the smoothing process, noise can be eliminated such that edges (i.e. step-like changes in density, which define boundaries among patterns of a plurality of different tissues of an object), which it is necessary to reproduce, may be kept sharp and no artifact may occur in the smoothed image. Also, noise can be eliminated quickly with simple operations.

Specifically, firstly, each of the picture elements in the bone image 43 is taken as a predetermined picture element, and the histogram of the image signal components of the bone image signal S1 is formed, which represent a plurality of the picture elements belonging to a predetermined region having the predetermined picture element in the middle.

Figure 3A:
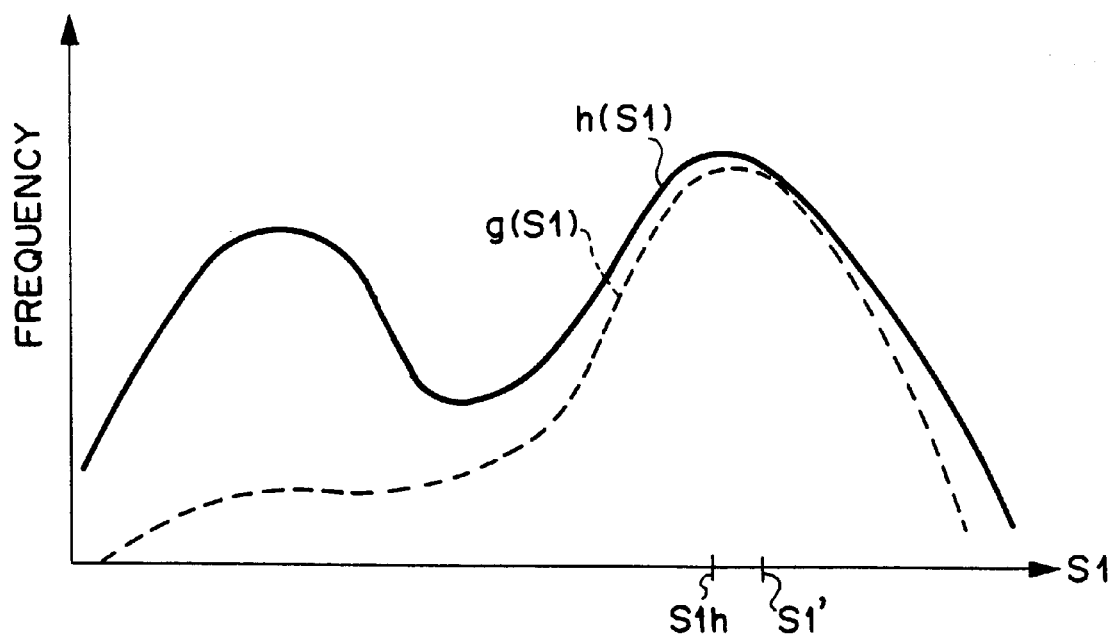
FIGS. 3A and 3B are graphs showing examples of histograms of image signal components, which image signal components represent a plurality of picture elements belonging to a predetermined region having a predetermined picture element in the middle.
Figure 3B:
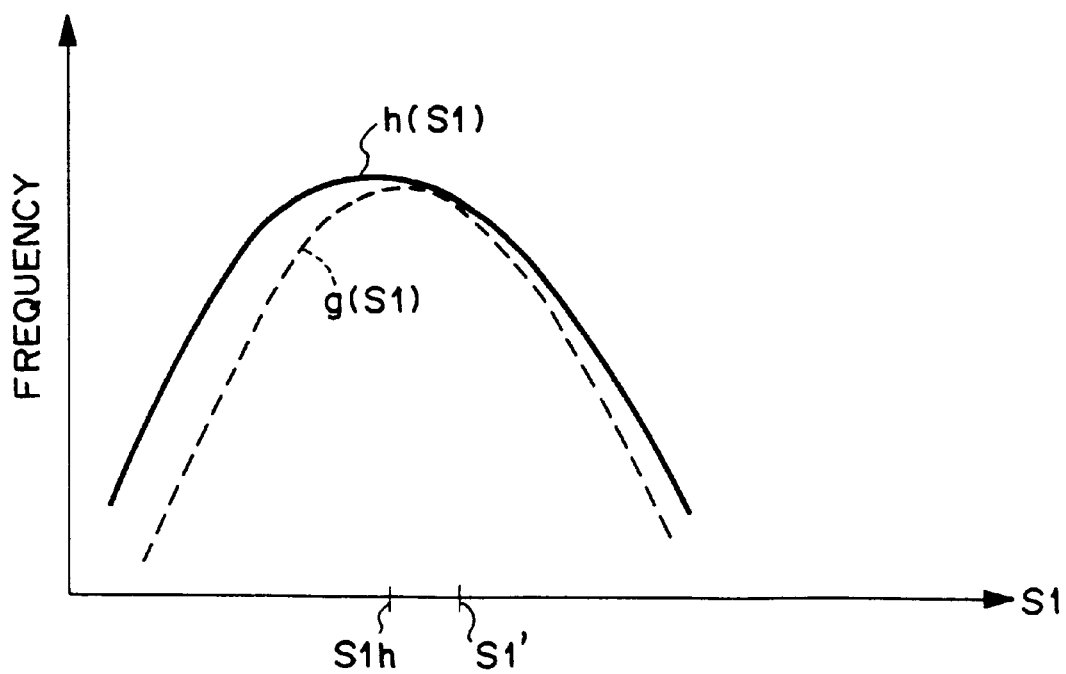
Figure 4:
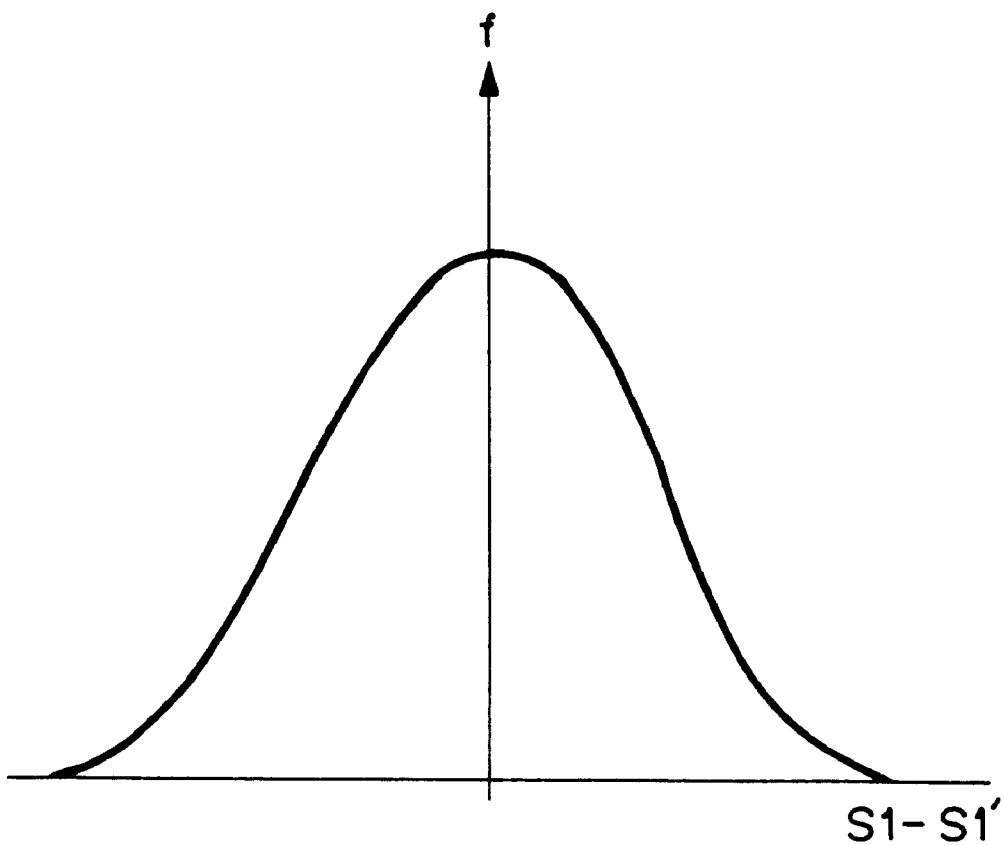
FIG. 4 is a graph showing an example of a function, in which the difference between the value of an image signal S1 and the value S1' of the image signal component representing a predetermined picture element located in the middle of a predetermined region serves as a variable.

FIGS. 3A and 3B are graphs showing examples of histograms of image signal components of the image signal S1, which image signal components represent a plurality of picture elements belonging to a predetermined region having a predetermined picture element in the middle. The image signal component representing the predetermined picture element has a value S1'. FIG. 4 is a graph showing an example of a function, in which the difference between the value of the image signal S1 and the value S1' of the image signal component representing the predetermined picture element located in the middle of the predetermined region serves as a variable.

The histograms shown in FIGS. 3A and 3B are represented by h(S1). Also, a function, the value of which decreases monotonously as the absolute value |S1−S1'| increases, e.g. the function shown in FIG. 4, is represented by f(S1−S1'). The values of a function g(S1) representing how frequently the values of image signal components of an image signal occur, which image signal has been processed, are calculated with the formula $$g(S1)=h(S1) \times f(S1-S1') \qquad (4)$$

In cases where the function h(S1) includes a plurality of projecting parts shown in FIG. 3A, the function g(S1) has the effects of extracting only of the projecting part, to which the image signal component having the value of S1' and representing the predetermined picture element belongs.

After the values of the function g(S1) have been calculated with Formula (4) shown above, the values of the image signal components of the image signal S1, which image signal components represent the picture elements belonging to the predetermined region, are weighted with the values of the function g(S1). A calculation is then made to find a mean-level value S1h of the weighted values of the image signal components of the image signal S1. Specifically, by way of example, the moment of first order of the function g(S1) is calculated with Formula (5) shown below.

$$S1h=\int g(S1) \times S1 dS1 / \int S1 dS1 \qquad (5)$$

The picture elements in the bone image 43 are successively taken as the predetermined picture element, and the processes with Formulas (4) and (5) are carried out for all of the picture elements in the bone image 43. In this manner, a smoothed image signal S1h, which represents a smoothed bone image 45, is obtained. (As an aid in facilitating the explanation, the same reference numeral is utilized to indicate both the value of the image signal component representing each picture element and the image signal representing the whole image.) As indicated by curve 52 in FIG. 2, the smoothed image signal S1h is formed by primarily eliminating the high spatial frequency components from the bone image signal S1. As shown in FIG. 3A, as for a picture element located in the vicinity of an edge, the smoothed image signal S1h has the mean-level value of the values belonging only to the projecting part, to which said picture element belongs. Therefore, edges in the bone image 43 can be kept sharp.

Thereafter, the superposition image signal SO, which is expressed as Formula (3) shown above and represents the superposition image 44, and the smoothed image signal S1h are weighted. The image signal components of the weighted smoothed image signal S1h are then subtracted from the image signal components of the weighted superposition image signal SO, which image signal components represent the image information stored at corresponding picture elements in the two X-ray images. In this manner, a soft tissue image signal S2' is obtained, which can be expressed as Formula (6) shown below.

$$S2' = SO - \frac{\left(1 + \frac{\mu_L^B}{\mu_H^B}\right)}{2 \cdot \left(\frac{\mu_L^B}{\mu_H^B} - \frac{\mu_L^T}{\mu_H^T}\right)} S1h + C'' \qquad (6)$$

where C" represents a bias component. The soft tissue image signal S2' represents a soft tissue image 46 shown in FIG. 1. The soft tissue image 46 has approximately the same image information as the soft tissue image expressed as Formula (2) shown above and includes less noise components than the soft tissue image expressed as Formula (2).

In the embodiment described above, the soft tissue image signal S2' is formed by smoothing the bone image signal S1 and subtracting the smoothed signal from the original image signal representing the original image. In cases where a bone image is to be reproduced, the soft tissue image signal S2 may be formed with Formula (2) shown above and then smoothed. The smoothed signal may then be subtracted from the original image signal representing the original image. In this manner, a bone image in which noise components have been reduced can be obtained.

Processing, which is substantially identical with the fundamental processing described above with reference to FIG. 1, will be described hereinbelow.

Figure 5:
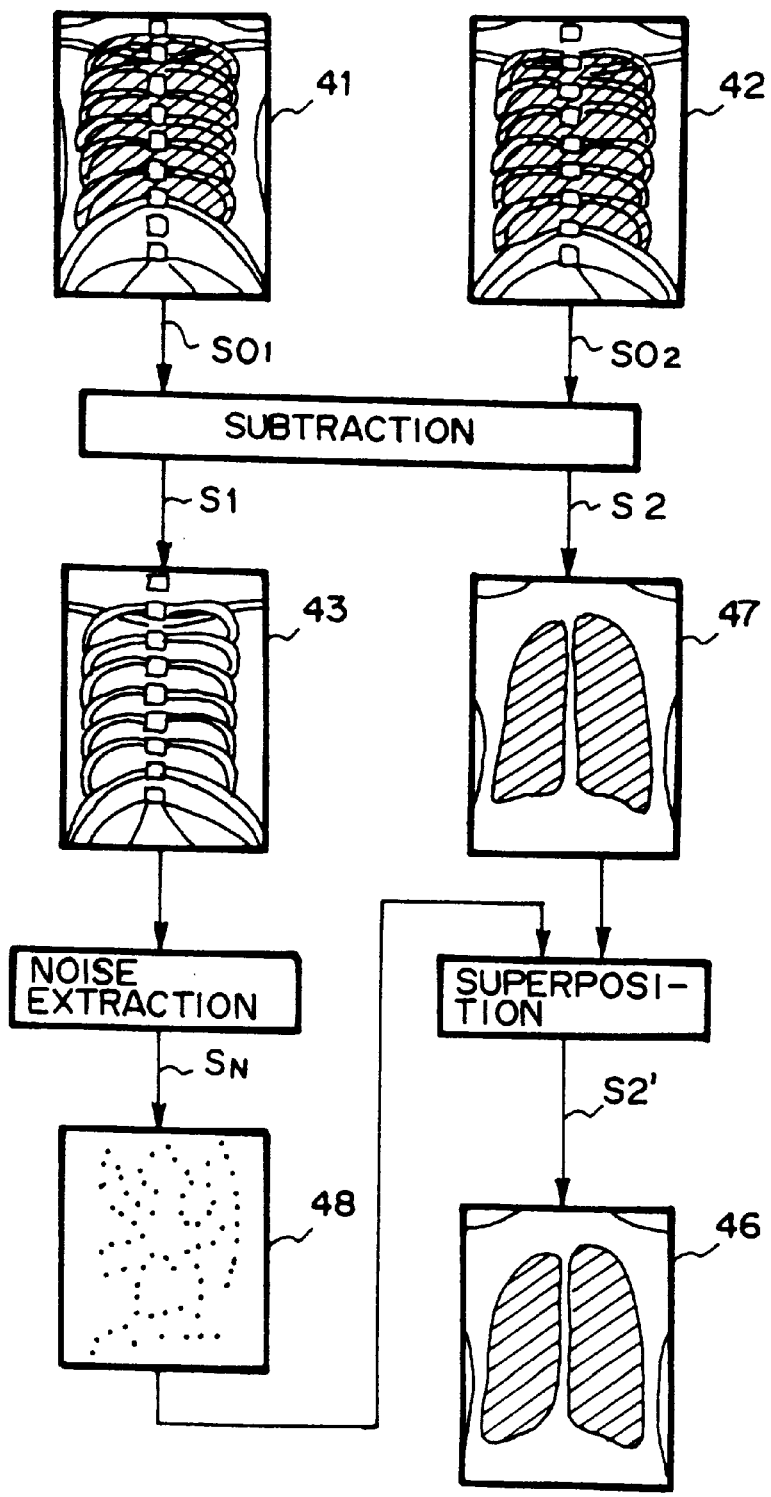
FIG. 5 is a flow chart showing the processing, which is substantially identical with the processing shown in FIG. 1 and is carried out in the image processing and displaying apparatus.

As an aid in explaining the substantially identical processing, FIG. 5 shows how the image processing and displaying apparatus 30 carries out the processing on the first image signal SO$_1$ representing the first X-ray image and the second image signal SO$_2$ representing the second X-ray image, which signals are stored in the internal memory of the image processing and displaying apparatus 30. In FIG. 5, similar elements are numbered with the same reference numerals with respect to FIG. 1.

With reference to FIG. 5, the bone image signal S1 representing the bone image 43 and the soft tissue image signal S2 representing a soft tissue image 47 are formed by carrying out calculations with Formulas (1) and (2) from the first image signal SO$_1$ representing the first X-ray image 41 and the second image signal SO$_2$ representing the second X-ray image 42.

Thereafter, in the same manner as that in the processing of FIG. 1, the smoothed image signal S1h representing the smoothed bone image, in which the noise components included in the bone image 43 have been reduced, is formed by processing the bone image signal S1 in accordance with Formulas (4) and (5). The image signal components of the smoothed image signal S1h are then subtracted from the image signal components of the bone image signal S1, which image signal components represent the image information stored at corresponding picture elements in the two X-ray images. In this manner, a noise signal S$_N$ representing a noise image 48, which is composed of only the noise components, is obtained. The noise signal S$_N$ can be expressed as $$S_N = S1 - S1h \qquad (7)$$

As indicated by the curve 53 in FIG. 2, the noise signal S$_N$ is composed of only the noise components included in the bone image 43. In the smoothed image signal S1h, even if the information representing the edges in the bone image 43 has a level of spatial frequency as high as that of the noise components, the information representing the edges will not be lost. Therefore, by carrying out the calculations with Formula (7) in order to find the difference between the bone image signal S1 and the smoothed image signal S1h, the noise signal S$_N$ can be obtained in which the information representing the edges has been completely canceled. Accordingly, the noise signal S$_N$ more accurately represents only the noise components of the bone image 43 than when a smoothing process was carried out such that the information representing the edges may be lost.

Thereafter, the noise signal S$_N$ and the soft tissue image signal S2 representing the soft tissue image 47 shown in FIG. 5 are weighted, and the image signal components of the weighted image signals are added to each other, which image signal components represent the image information stored at corresponding picture elements in the two images. In this manner, a soft tissue image signal S2' is obtained, which represents a soft tissue image 46 shown in FIG. 5. The soft tissue image 46 has approximately the same image information as the soft tissue image 47 and includes less noise components than the soft tissue image 47. In this embodiment, the calculations are carried out with Formula (8) shown below.

$$S2' = \left\{ \left(1 + \frac{\mu_L^T}{\mu_H^T}\right) \cdot S2 + \left(1 + \frac{\mu_L^B}{\mu_H^B}\right) S_N \right\} / 2 \cdot \left(\frac{\mu_L^B}{\mu_H^B} - \frac{\mu_L^T}{\mu_H^T}\right) \qquad (8)$$

Therefore, the noise components can be reduced even further.

As described above, the processing of FIG. 5 is substantially identical with the processing of FIG. 1. The reason for this will be described hereinbelow.

The soft tissue image signal S2 expressed as Formula (2) and the noise signal S$_N$ expressed as Formula (7) are substituted into Formula (8). The bias component, such as C' in Formula (2), is used in order to adjust the image density of the whole image which is obtained ultimately (and in order to adjust the luminance in cases where the image is displayed on a CRT display device, or the like). Therefore, in the operations described below, the bias component is not taken into consideration.

Substitution of Formulas (2) and (7) into Formula (8) yields Formula (9) shown below.

$$S2' = \left\{ \left(1 + \frac{\mu_L^T}{\mu_H^T}\right) \cdot \left(\frac{\mu_L^B}{\mu_H^B} \cdot S0_2 - S0_1\right) + \left(1 + \frac{\mu_L^B}{\mu_H^B}\right) \cdot (S1 - S1h) \right\} / 2 \cdot \left(\frac{\mu_L^B}{\mu_H^B} - \frac{\mu_L^T}{\mu_H^T}\right) \quad (9)$$

Substitution of the bone image signal S1 expressed as Formula (1) into Formula (9) (with the bias component being ignored) yields Formula (10) shown below.

$$S2' = \left\{ \left(1 + \frac{\mu_L^T}{\mu_H^T}\right) \cdot \left(\frac{\mu_L^B}{\mu_H^B} \cdot S0_2 - S0_1\right) + \left(1 + \frac{\mu_L^B}{\mu_H^B}\right) \cdot \left(S0_1 - \frac{\mu_L^B}{\mu_H^B} \cdot S0_2 - S1h\right) \right\} / 2 \cdot \left(\frac{\mu_L^B}{\mu_H^B} - \frac{\mu_L^T}{\mu_H^T}\right) \quad (10)$$

Transforming and rearranging Formula (10) yield Formula (11) shown below.

$$S2' = (S0_1 + S0_2)/2 - \frac{1 + \frac{\mu_L^B}{\mu_H^B}}{2\left(\frac{\mu_L^B}{\mu_H^B} - \frac{\mu_L^T}{\mu_H^T}\right)} \cdot S1h \quad (11)$$

Substituting Formula (3) into Formula (11) yields Formula (12) shown below.

$$S2' = S0 - \frac{1 + \frac{\mu_L^B}{\mu_H^B}}{2\left(\frac{\mu_L^B}{\mu_H^B} - \frac{\mu_L^T}{\mu_H^T}\right)} \cdot S1h \quad (12)$$

Formula (12) is identical with Formula (6), except for the bias component. Specifically, in the processing of FIG. 1 and the processing of FIG. 5, substantially identical processing is carried out.

Figure 6:
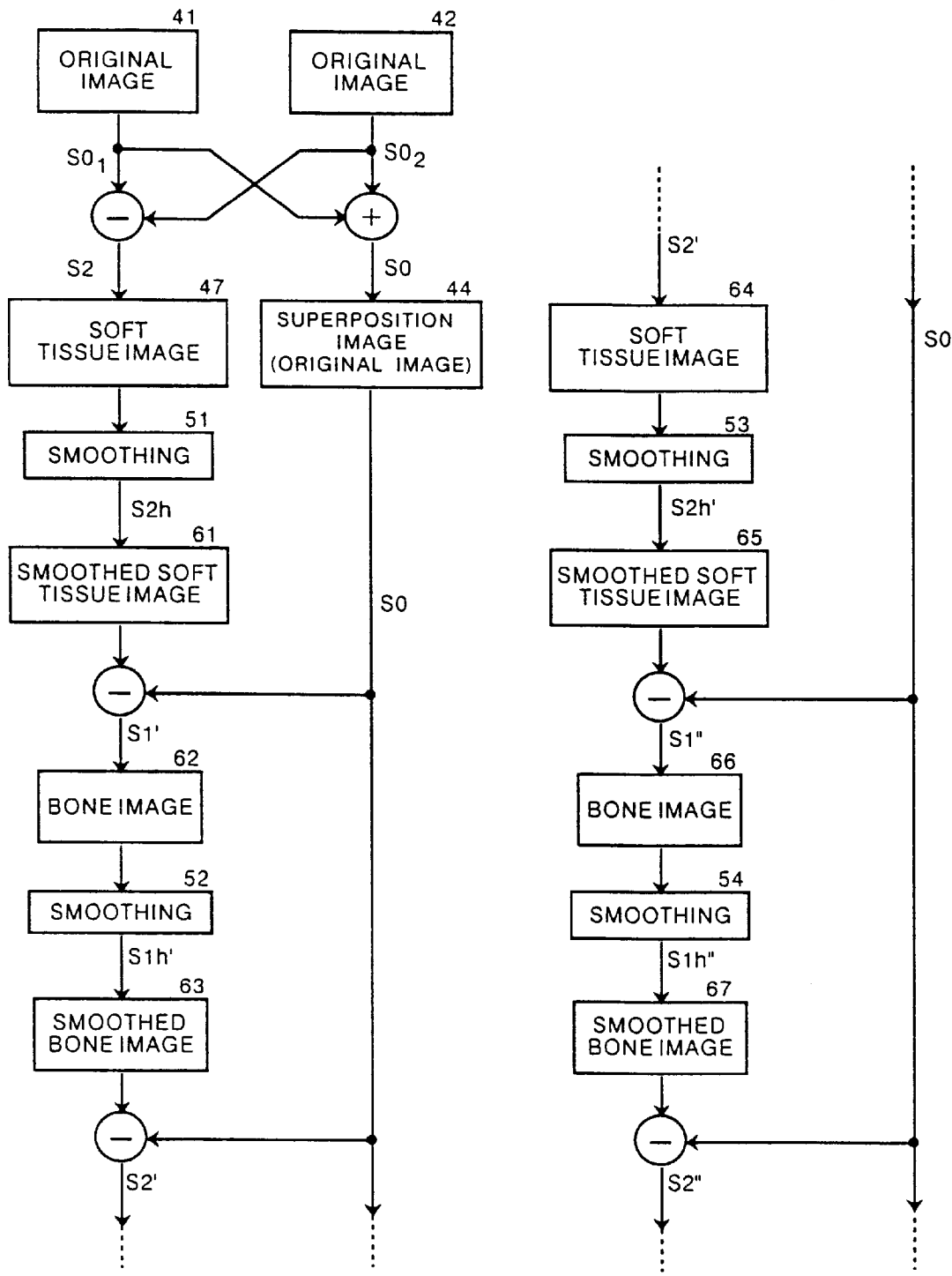
FIG. 6 is a flow chart showing the different fundamental processing.

FIG. 6 is a flow chart showing the different fundamental processing, which is based upon the processing of FIG. 1. FIGS. 7A through 7M are graphs showing the profiles of the images, which are shown in FIG. 6, along a predetermined direction.

In FIG. 6, similar elements are numbered with the same reference numerals with respect to FIG. 1 or FIG. 5.

Figure 7A:
FIG. 7A through 7M are graphs showing the profiles of the images, which are shown in FIG. 6, along a predetermined direction.
Figure 7B:
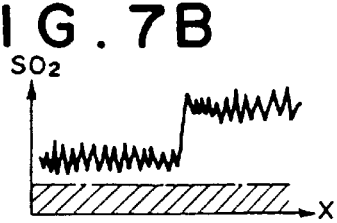

FIGS. 7A and 7B show the profiles of the first X-ray image 41 and the second X-ray image 42, which are original images. Specifically, FIG. 7A shows how the values of the image signal components of the first image signal SO$_1$ representing the first X-ray image 41 are distributed, which image signal components represent the picture elements located along a predetermined direction (x direction) in the first X-ray image 41. FIG. 7B shows how the values of the image signal components of the second image signal SO$_2$ representing the second X-ray image 42 are distributed, which image signal components represent the picture elements located along the predetermined direction (x direction) in the second X-ray image 42. The levels of the first image signal SO$_1$ and the second image signal SO$_2$ are different from each other. However, each of the first image signal SO$_1$ and the second image signal SO$_2$ is composed of the image signal components, which represent the soft tissue patterns (corresponding to the hatched region in FIG. 7A or FIG. 7B) and have approximately uniform values, the image signal components, which represent the bone patterns and have values changing step-wise, and the random noise components. These three types of image signal components are superposed one upon another.

The weighted subtraction process (indicated by "−" in FIG. 6) is carried out with Formula (2) on the first image signal SO$_1$ representing the first X-ray image 41 (the original image) and the second image signal SO$_2$ representing the second X-ray image 42 (the original image), and the soft tissue image signal S2 representing the soft tissue image 47 is thereby formed. Also, the addition process (indicated by "+" in FIG. 6) is carried out with Formula (3) on the first image signal SO$_1$ and the second image signal SO$_2$, and the superposition image signal SO representing the superposition image 44 is thereby formed.

Figure 7C:
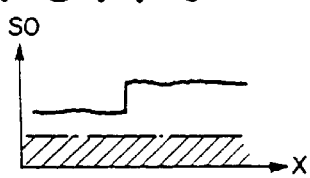

FIG. 7C shows how the values of the image signal components of the superposition image signal SO are distributed. As in the first image signal SO$_1$ shown in FIG. 7A and the second image signal SO$_2$ shown in FIG. 7B, the superposition image signal SO is composed of the image signal components, which represent the soft tissue patterns (corresponding to the hatched region in FIG. 7) and have approximately uniform values, the image signal components, which represent the bone patterns and have values changing step-wise, and the random noise components. These three types of image signal components are superposed one upon another. However, the superposition image signal SO includes less noise components than the first image signal SO$_1$ shown in FIG. 7A and the second image signal SO$_2$ shown in FIG. 7B.

Figure 7D:
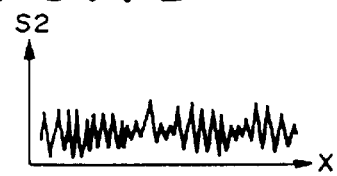

FIG. 7D shows how the values of the image signal components of the soft tissue image signal S2, which has been formed with Formula (2), are distributed. The soft tissue image signal S2 is primarily composed of the image signal components, which represent the soft tissue patterns and have approximately uniform values. However, the soft tissue image signal S2 includes more random noise components than the first image signal SO$_1$ shown in FIG. 7A and the second image signal SO$_2$ shown in FIG. 7B.

Figure 7E:
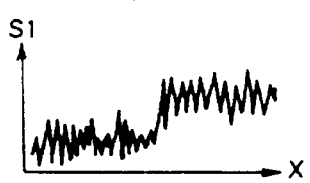
Figure 7F:

FIG. 7E shows how the values of the image signal components of the bone image signal S1, which may be formed with Formula (1), are distributed. (In this embodiment, the bone image signal S1 need not be formed.) The bone image signal S1 is primarily composed of the image signal components, which represent the bone patterns and have values changing step-wise. However, as in the soft tissue image signal S2 shown in FIG. 7D, the bone image signal S1 includes more random noise components than the first image signal SO$_1$ shown in FIG. 7A and the second image signal SO$_2$ shown in FIG. 7B.

As illustrated in FIG. 6, a smoothing process 51 is carried out on the soft tissue image signal S2, which represents the soft tissue image 47 and is distributed as shown in FIG. 7D. From the smoothing process 51, a smoothed soft tissue image signal S2h is obtained, which represents a smoothed soft tissue image 61 and is distributed in the pattern shown in FIG. 7F. With the smoothing process 51, the spatial frequency components higher than a frequency of, for example, 1.0 cycle/mm are eliminated from the soft tissue image signal S2 representing the soft tissue image 47.

Figure 7G:

Thereafter, the superposition image signal SO and the smoothed soft tissue image signal S2h are weighted, and the weighted smoothed soft tissue image signal S2h is subtracted from the weighted superposition image signal S0. In this manner, a bone image signal S1' is obtained, which represents a bone image 62. As illustrated in FIG. 7G, the bone image signal S1' includes less random noise components than the bone image signal S1 shown in FIG. 7E. However, the bone image signal S1' slightly includes the high spatial frequency components of the soft tissue image 47 due to the smoothing process carried out on the soft tissue image 47.

A smoothing process 52 is then carried out on the bone image signal S1', which has been formed in the manner described above. With the smoothing process 52, patterns having low contrast and falling within the spatial frequency region higher than, for example, 0.5 cycle/mm are eliminated from the bone image 62 (i.e. small changes in the bone image signal S1' are eliminated). For this purpose, by way of example, the bone image signal S1' may be processed with a filter described below. Specifically, a window having an area corresponding to 0.5 cycle/mm is determined for a predetermined picture element $P_0$. From the image signal components of the bone image signal S1' representing the picture elements belonging to the window, the image signal components are then found the values of which fall within the range of:

the value of an image signal component $S1_0'$ representing the predetermined picture element $P_0$ ± a predetermined value.

Figure 7H:
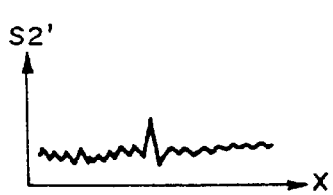
Figure 7I:
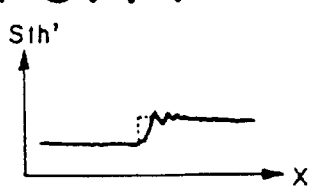
Figure 7J:
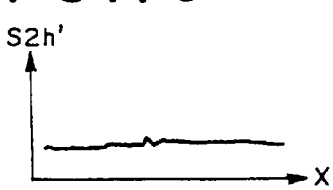

Thereafter, the mean value of the image signal components, which have thus been found, is calculated and employed as the value of a new image signal component $S1_0'$ representing the predetermined picture element $P_0$. With the smoothing process 52, a smoothed bone image signal S1h' is obtained which represents a smoothed bone image 63. As illustrated in FIG. 7I, in the smoothed bone image signal S1h', the noise components have been reduced. Also, the high spatial frequency components of the soft tissue image 47 due to the smoothing process carried out on the soft tissue image 47 have been reduced. However, the rising part of the smoothed bone image signal S1h' becomes unsharp.

Thereafter, the superposition image signal S0 and the smoothed bone image signal S1h' are weighted, and weighted smoothed bone image signal S1h' is subtracted from the weighted superposition image signal S0. In this manner, a soft tissue image signal S2' is obtained which represents a soft tissue image 64. As illustrated in FIG. 7H, the soft tissue image signal S2' includes less noise components than the soft tissue image signal S2 shown in FIG. 7D. Also, because the rising part of the smoothed bone image signal S1h' shown in FIG. 7I is unsharp, the information representing the corresponding part of the bone image is included as noise in the soft tissue image signal S2'. However, the level of random noise and the level of the information, which represents the bone image and constitutes noise, are very low. Therefore, a series of the processes may be finished in this step. The soft tissue image signal S2' may be fed into the CRT display device 32 of the image processing and displaying apparatus 30 shown in FIG. 10, and a visible image may be reproduced from the soft tissue image signal S2' and displayed on the CRT display device 32.

However, in this embodiment, the fundamental processes shown in FIG. 1 or FIG. 5 are repeated even further such that an image having better image quality may be obtained.

After the soft tissue image signal S2' representing the soft tissue image 64 has been formed, a smoothing process 53 is carried out on the soft tissue image signal S2'. From the smoothing process 53, a smoothed soft tissue image signal S2h' is obtained, which represents a smoothed soft tissue image 65 and is distributed in the pattern shown in FIG. 7J. With the smoothing process 53, the spatial frequency components higher than a frequency of, for example, 1.5 cycle/mm are eliminated from the soft tissue image signal S2'.

Figure 7K:

Thereafter, the superposition image signal S0 and the smoothed soft tissue image signal S2h' are weighted, and the weighted smoothed soft tissue image signal S2h' is subtracted from the weighted superposition image signal S0. In this manner, a bone image signal S1" is obtained, which represents a bone image 66. As illustrated in FIG. 7K, the bone image signal S1" includes less random noise components and less information, which represents the soft tissue image and constitutes noise, than the bone image signal S1' shown in FIG. 7G. In cases where a bone image is to be reproduced, a visible image may be reproduced from the bone image signal S1" and reproduced on the CRT display device 32.

In this embodiment, a smoothing process 54 is then carried out on the bone image signal S1", which has been formed in the manner described above. From the smoothing process 54, a smoothed bone image signal S1h" is obtained, which represents a smoothed bone image 67 and is distributed in the pattern shown in FIG. 7M. With the smoothing process 54, patterns having low contrast and falling within the spatial frequency region higher than, for example, 1.0 cycle/mm are eliminated from the bone image 66.

Figure 7L:
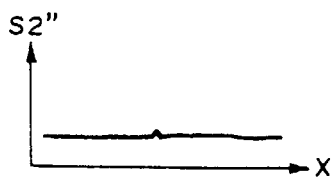
Figure 7M:
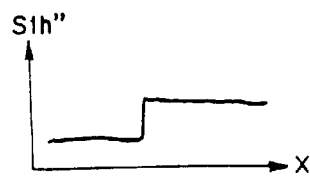

Thereafter, the superposition image signal S0 and the smoothed bone image signal S1h" are weighted, and weighted smoothed bone image signal S1h" is subtracted from the weighted superposition image signal S0. In this manner, a soft tissue image signal S2" is obtained. As illustrated in FIG. 7L, the soft tissue image signal S2" includes less random noise components and less information, which represents the bone image and constitutes noise, than the soft tissue image signal S2" shown in FIG. 7H.

In the manner described above, the smoothing processes and the weighted subtraction processes with respect to the superposition image signal S0 (the original image signal) are carried out repeatedly such that the bone images and soft tissue images, in which noise has been reduced sequentially, may be obtained alternately.

The number of repetitions of the processes is set in the manner described below.

Specifically, the number of repetitions is determined in accordance with the S value, which has been calculated from the image signals in the manner described above, and by making reference to a table shown in FIG. 11.

More specifically, in cases where the S value is large, the dose of radiation was small, and the level of noise contained in the original image is high. In the Table shown in FIG. 11, N represents the number of repetitions for obtaining the soft tissue image, and M represents the number of repetitions for obtaining the bone image. As illustrated in the table of FIG. 11, the number of repetitions is set to be large as the S value becomes large.

In this manner, the number of repetitions is determined in accordance with the S value, i.e. the dose of radiation. Therefore, the number of repetitions is set to be large as the S value becomes large, i.e. as the level of noise becomes high. As a result, noise can be reduced even further in the soft tissue image and the bone image, which are obtained ultimately. Also, the number of repetitions is set to be small as the S value becomes small, i.e. as the level of noise becomes low. As a result, noise does not disappear completely from the obtained image, and the soft tissue image and the bone image, in which an appropriate level of noise remains and which give a natural feeling, can be obtained.

Figure 8:
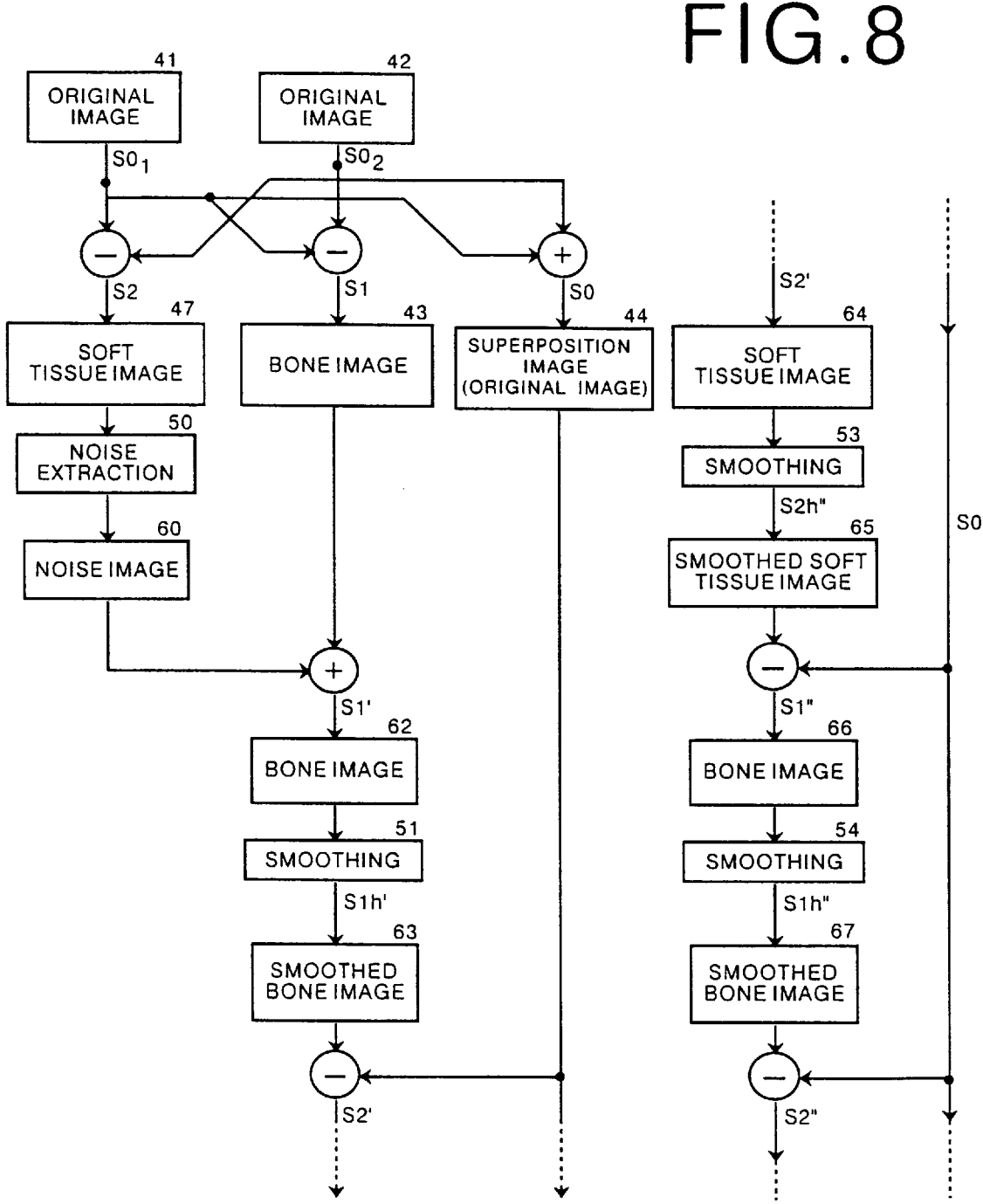
FIG. 8 is a flow chart showing the processing, which is substantially identical with the processing shown in FIG. 6.

FIG. 8 is a flow chart showing the processing, which is substantially identical with the processing shown in FIG. 6. In FIG. 8, similar elements are numbered with the same reference numerals with respect to FIG. 6 and the other drawings.

In the processing of FIG. 8, the series of the processes for forming the bone image 62 in the processing of FIG. 6 (which processes correspond to the processes described above with reference to FIG. 1, except that the bone image and the soft tissue image are interchanged with each other) are replaced by the processes described above with reference to FIG. 5. In the processing of FIG. 8, the bone image and the soft tissue image in the processes shown in FIG. 5 are interchanged with each other. As described above, the processing of FIG. 8 is substantially identical with the processing of FIG. 6.

In the processing of FIG. 8, only the initial processes in the processing of FIG. 6 are replaced by the processes described above with reference to FIG. 5. Such replacement may be carried out at an arbitrary stage of the processes carried out repeatedly. Such embodiments are substantially identical with the processing of FIG. 6. The method of forming an energy subtraction image in accordance with the present invention embraces various such, substantially identical embodiments wherein at least one stage of the processes is modified.

A different embodiment of the method of forming an energy subtraction image in accordance with the present invention will be described hereinbelow with reference to FIG. 1.

In this embodiment, in the fundamental processing of FIG. 1, which is carried out in the image processing and displaying apparatus 30, when the smoothing process is carried out on the bone image signal S1 and the smoothed image signal S1h, which represents the smoothed bone image 45, is thereby formed, the degree of the smoothing process is altered in accordance with the S value described above. Specifically, in cases where the S value is small, the dose of radiation at the time, at which the original image signals were obtained, is large, and the level of noise contained in the original images is low. Therefore, the degree of the smoothing process is set to be low as the S value becomes small, and the degree of blurring of the smoothed bone image 45 is thereby rendered low. Also, the degree of the smoothing process is set to be high as the S value becomes large, and the degree of blurring of the smoothed bone image 45 is thereby rendered high. For example, the degree of the smoothing process may be set to be small in the manner described below. Specifically, in cases where the unsharp mask processing is carried out as the smoothing process, the size of the unsharp mask may be set to be small as the S value becomes small, or the degree of weighting of the middle picture element of the unsharp mask may be set to be high. In cases where the median filter is employed for the smoothing process, the median value of the median filter may be weighted. In cases where the V-filter is employed for the smoothing process, the degree of weighting of the mean value of the values of the image signal components corresponding to the small region, which is associated with the smallest variance, may be set to be high. In cases where Fourier transformation is carried out for the smoothing process, the degree of removal of high spatial frequency components may be set to be low.

Also, as the smoothing process, a smoothing process utilizing the aforesaid filter adaptive to a histogram may be carried out. In cases where the filter adaptive to a histogram is employed, the degree of weighting with the function g(S1) in the processes according to Formulas (4) and (5) shown above may be set to be high. In this manner, the blurring of the edges in the bone image can be restricted.

Thereafter, as described above with reference to FIG. 1, the superposition image signal SO, which is expressed as Formula (3) shown above and represents the superposition image 44, and the smoothed image signal S1h are weighted and subtracted from each other in accordance with Formula (6) shown above. In this manner, the soft tissue image 46 shown in FIG. 1 is obtained.

The soft tissue image signal S2', which has been obtained with Formula (6) shown above, is fed into the CRT display device 32 of the image processing and displaying apparatus 30. A visible image is reproduced from the soft tissue image signal S2' and displayed on the CRT display device 32.

In this embodiment, the soft tissue image signal S2' is formed by smoothing the bone image signal S1 and subtracting the smoothed signal from the original image signal representing the original image. In cases where a bone image is to be reproduced, the soft tissue image signal S2 may be formed with Formula (2) shown above and then smoothed. The smoothed signal may then be subtracted from the original image signal representing the original image. In this manner, a bone image in which noise components have been reduced can be obtained. In such cases, the degree of the smoothing process carried out on the soft tissue image signal S2 is set to be low as the S value becomes small. In this manner, the degree of blurring of the smoothed soft tissue image can be kept low, and the bone image having image quality enhanced even further can be obtained.

Also, in the processing of FIG. 5, which is substantially identical with the fundamental processing described above with reference to FIG. 1, in the same manner as that in the processing of FIG. 1, the smoothed image signal S1h representing the smoothed bone image, in which the noise components included in the bone image 43 have been reduced, is formed by processing the bone image signal S1 in accordance with Formulas (4) and (5). In such cases, the degree of the smoothing process is set to be low as the S value becomes small. As a result, the edge information is retained to a high extent in the smoothed image signal S1h. Therefore, with Formula (7) shown above, the noise signal $S_N$, which more accurately represents only the noise components of the bone image 43, can be obtained. Accordingly, the bone image or the soft tissue image, in which only the noise components have been eliminated, can be obtained.

Further, in the processing of FIG. 6, the degrees of the smoothing processes 51, 52, 53, and 54 are altered in accordance with the S value in the manner described below.

Specifically, in the processing of FIG. 6, as in the embodiments described above with reference to FIGS. 1 and 5, the degree of the smoothing process is altered in accordance with the S value. For example, in cases where the number of repetitions of the processes described above is three, the degree of the smoothing process is altered in the manner shown in a table of FIG. 12. More specifically, in cases where the S value falls within the range of 0 to 50, no smoothing process is carried out. In cases where the S value falls within the range of 50 to 100, the second and third smoothing processes are not carried out. In cases where the S value falls within the range of 100 to 200, the third smoothing process is not carried out. In cases where the S value is larger than 200 and the level of noise is thus very high, all of the three smoothing processes are carried out. In this manner, in cases where the dose of radiation is large, i.e.

in cases where the level of noise is low, the degree of blurring of the image with the smoothing process can be kept low, and the soft tissue image and the bone image having good image quality with little blurring can be obtained.

The setting of the degree of the smoothing process is not limited to the setting with the table shown in FIG. 12. For example, in cases where the unsharp mask processing is employed as the smoothing process, the size of the unsharp mask may be set to be small as the S value becomes small.

Specifically, in cases where the S value falls within the range of 0 to 50, an unsharp mask having a size of 3×3 may be utilized. In cases where the S value falls within the range of 50 to 100, an unsharp mask having a size of 5×5 may be utilized. In cases where the S value falls within the range of 100 to 150, an unsharp mask having a size of 7×7 may be utilized. In cases where the S value is larger than 200, an unsharp mask having a size of 9×9 may be utilized. In this manner, the degree of blurring may be set to be low as the S value becomes small. Alternatively, an unsharp mask having the same size may be utilized regardless of the level of the S value, and the degree of weighting of the middle picture element of the unsharp mask may be set to be high as the S value becomes small.

In the embodiments described above wherein the degree of the smoothing process is altered in accordance with the S value, as illustrated in FIG. 11, the number of repetitions of the processes may be determined in accordance with the S value.

Also, in the processing of FIG. 8, the degree of the smoothing process is altered in accordance with the S value.

In the aforesaid various embodiments of the method of forming an energy subtraction image in accordance with the present invention, a soft tissue image or a bone image is formed from X-ray images of the chest of a human body. However, the method of forming an energy subtraction image in accordance with the present invention is not limited to the formation of the soft tissue image or the bone image, but is applicable widely when either one or both of two images are to be obtained, in which the patterns of two different tissues of a single object have been emphasized or only such patterns are illustrated. For example, two such images may be an image, in which the patterns of mammary glands have been emphasized, and an image, in which the pattern of a malignant tumor has been emphasized.

Also, in the aforesaid various embodiments of the method of forming an energy subtraction image in accordance with the present invention, stimulable phosphor sheets are used. However, the method for forming an energy subtraction image in accordance with the present invention is also applicable when other recording media, such as X-ray film (ordinarily combined with intensifying screens), are used.

Further, in the aforesaid various embodiments of the method of forming an energy subtraction image in accordance with the present invention, the S value is calculated from the image signals. Alternatively, information, which represents the dose of radiation delivered in the operation for recording the radiation image of the object, may be directly fed into the image processing and displaying apparatus 30. As another alternative, information representing the image recording conditions, under which the radiation image of the object was recorded, may be fed into the image processing and displaying apparatus 30, and the dose of radiation delivered at the time of the image recording may be presumed from the image recording conditions.

What is claimed is:

1. A method of forming an energy subtraction image, comprising the steps of:

i) after a plurality of radiation images of an object are formed with a plurality of kinds of radiation having different energy distributions, the object being constituted of a plurality of tissues exhibiting different levels of radiation absorptivity, and a plurality of original image signals, each of which represents one of the radiation images, are then detected, carrying out a first process for obtaining a first image signal, which represents a first image primarily composed of patterns of first tissues of the object, from the plurality of the original image signals, ii) thereafter carrying out a second process, which comprises the steps of:

a) obtaining a first smoothed image signal by processing the first image signal, the first smoothed image signal representing a first smoothed image in which noise components of the first image have been reduced, and b) obtaining a second image signal by subtracting the first smoothed image signal from an original image signal, the second image signal representing a second image primarily composed of patterns of second tissues of the object, iii) thereafter carrying out a third process, which comprises the steps of:

a) obtaining a second smoothed image signal by processing the second image signal, the second smoothed image signal representing a second smoothed image in which noise components of the second image have been reduced, and b) obtaining a new first image signal by subtracting the second smoothed image signal from an original image signal, the new first image signal representing a new first image primarily composed of the patterns of the first tissues of the object, and iv) thereafter repeating the following a predetermined number of times:

a) a new second process for obtaining a new second image signal by carrying out the second process in which the new first image signal having been obtained from the third process is taken as the first image signal in the second process, the new second image signal formed by the new second process representing a new second image primarily composed of the patterns of the second tissues of the object, and b) a new third process for obtaining a new first image signal by carrying out the third process in which the new second image signal is taken as the second image signal in the third process, the new first image signal obtained from the new third process representing a new first image primarily composed of the patterns of the first tissues of the object, wherein the improvement comprises determining the number of repetitions of the new second process and the new third process in accordance with a dose of radiation at the time, at which the original image signals were obtained.

2. A method of forming an energy subtraction image, comprising the steps of:

i) carrying out the processes in the method of forming an energy subtraction image as defined in claim 1, and ii) thereafter obtaining a new second image signal by carrying out the second process or the new second process in which the new first image signal having been obtained from the third process or the new third process is taken as the first image signal in the second process or the new second process, the new second image signal thus most recently obtained representing a new second image primarily composed of the patterns of the second tissues of the object.

3. A method of forming an energy subtraction image, comprising the steps of:

i) after a plurality of radiation images of an object are formed with a plurality of kinds of radiation having different energy distributions, the object being constituted of a plurality of tissues exhibiting different levels of radiation absorptivity with respect to the plurality of kinds of radiation, and a plurality of original image signals, each of which represents one of the radiation images, are then detected, obtaining a first image signal, which represents a first image primarily composed of patterns of first tissues of the object, from the plurality of the original image signals, ii) obtaining a first smoothed image signal by carrying out a smoothing process on the first image signal, the first smoothed image signal representing a first smoothed image in which noise components of the first image have been reduced or eliminated, and iii) obtaining a second image signal by subtracting the first smoothed image signal from an original image signal, the second image signal representing a second image primarily composed of patterns of second tissues of the object, wherein the improvement comprises setting the degree of the smoothing process, which is carried out on the first image signal, to be low as a dose of radiation at the time, at which the original image signals were obtained, becomes large.

4. A method of forming an energy subtraction image, comprising the steps of:

i) after a plurality of radiation images of an object are formed with a plurality of kinds of radiation having different energy distributions, the object being constituted of a plurality of tissues exhibiting different levels of radiation absorptivity with respect to the plurality of kinds of radiation, and a plurality of original image signals, each of which represents one of the radiation images, are then detected, carrying out a first process for obtaining a first image signal, which represents a first image primarily composed of patterns of first tissues of the object, from the plurality of the original image signals, ii) thereafter carrying out a second process, which comprises the steps of:

a) obtaining a first smoothed image signal by processing the first image signal, the first smoothed image signal representing a first smoothed image in which noise components of the first image have been reduced, and b) obtaining a second image signal by subtracting the first smoothed image signal from an original image signal, the second image signal representing a second image primarily composed of patterns of second tissues of the object, and iii) thereafter carrying out a third process, which comprises the steps of:

a) obtaining a second smoothed image signal by carrying out a smoothing process on the second image signal, the second smoothed image signal representing a second smoothed image in which noise components of the second image have been reduced, and b) obtaining a new first image signal by subtracting the second smoothed image signal from an original image signal, the new first image signal representing a new first image primarily composed of the patterns of the first tissues of the object, wherein the improvement comprises setting the degree of the smoothing process, which is carried out on the first image signal, and the degree of the smoothing process, which is carried out on the second image signal, to be low as a dose of radiation at the time, at which the original image signals were obtained, becomes large.

5. A method of forming an energy subtraction image comprising the steps of:

i) carrying out the processes in the method of forming an energy subtraction image as defined in claim 4, and ii) thereafter repeating the following a predetermined number of times:

a) a new second process for obtaining a new second image signal by carrying out the second process in which the new first image signal having been obtained from the third process is taken as the first image signal in the second process, the new second image signal formed by the new second process representing a new second image primarily composed of the patterns of the second tissues of the object, and b) a new third process for obtaining a new first image signal by carrying out the third process in which the new second image signal is taken as the second image signal in the third process, the new first image signal obtained from the new third process representing a new first image primarily composed of the patterns of the first tissues of the object.

6. A method as defined in claim 5 wherein the number of repetitions of the new second process and the new third process is determined in accordance with a dose of radiation at the time, at which the original image signals were obtained.

7. A method of forming an energy subtraction image, comprising the steps of:

i) carrying out the processes in the method of forming an energy subtraction image as defined in claim 4, 5, or 6, and ii) thereafter obtaining a new second image signal by carrying out the second process or the new second process in which the new first image signal having been obtained from the third process or the new third process is taken as the first image signal in the second process or the new second process, the new second image signal thus most recently obtained representing a new second image primarily composed of the patterns of the second tissues of the object.

* * * * *